US009782778B1

(12) United States Patent
Drynkin et al.

(10) Patent No.: US 9,782,778 B1
(45) Date of Patent: Oct. 10, 2017

(54) LABORATORY TUBE PRESENTATION APPARATUS FOR RAISING A ROW OF TUBES CONTAINED IN A RACK OF TUBES

(71) Applicants: Alexander V. Drynkin, San Ramon, CA (US); David B. Miller, Orinda, CA (US); William M. Hess, Pinole, CA (US)

(72) Inventors: Alexander V. Drynkin, San Ramon, CA (US); David B. Miller, Orinda, CA (US); William M. Hess, Pinole, CA (US)

( * ) Notice: Subject to any disclaimer, the term of this patent is extended or adjusted under 35 U.S.C. 154(b) by 0 days.

(21) Appl. No.: 15/008,382

(22) Filed: Jan. 27, 2016

Related U.S. Application Data

(60) Provisional application No. 62/113,320, filed on Feb. 6, 2015.

(51) Int. Cl.
*B01L 9/06* (2006.01)
*B65B 43/58* (2006.01)
*B65B 43/48* (2006.01)
*G01N 35/04* (2006.01)

(52) U.S. Cl.
CPC ............ *B01L 9/06* (2013.01); *B01L 2200/025* (2013.01); *B01L 2300/0851* (2013.01); *B65B 43/48* (2013.01); *G01N 2035/041* (2013.01)

(58) Field of Classification Search
CPC ...... B01L 9/06; G01N 2035/041; B65B 43/48
See application file for complete search history.

(56) References Cited

U.S. PATENT DOCUMENTS 2,373,026 A * 4/1945 Guyer .................... G01N 9/02
73/32 R

FOREIGN PATENT DOCUMENTS

DE WO 2014072019 A2 * 5/2014 ............ B65B 3/006

OTHER PUBLICATIONS

Machine Generated English translation of WO 2014072019, Wansel et al., May 15, 2014, pp. 1-10.*

* cited by examiner

*Primary Examiner* — P. Kathryn Wright

(57) ABSTRACT

A laboratory tube presentation unit for removal of a selected laboratory tube in a tube rack having multiple rows of laboratory tubes by raising the row of tubes in which the selected tube is located, the rack having tube wells and a rectangular bottom with a hole in each well, the unit including a selector assembly having a displaceable actuator assembly with a row of lift pins that are alignable under a select row of holes in the tube wells that correspond to a row of tubes having the selected tube in the tube rack seated on the top deck, the actuator assembly carriage having further an actuator with a manual transport shift and a lift mechanism that raises the row of lift pins under the select row of holes in the tube wells having the particular tube to be removed.

9 Claims, 7 Drawing Sheets

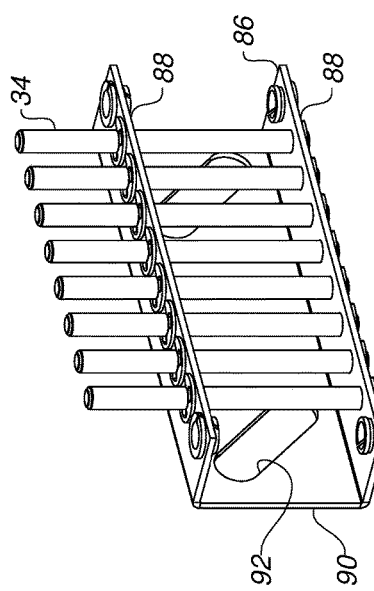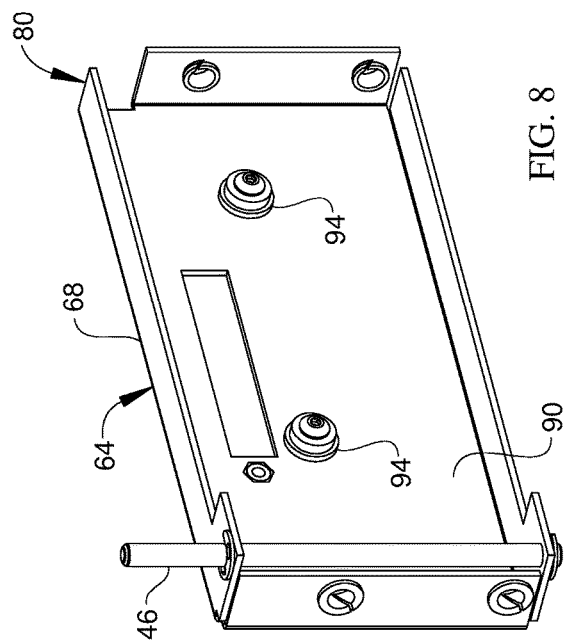

LABORATORY TUBE PRESENTATION APPARATUS FOR RAISING A ROW OF TUBES CONTAINED IN A RACK OF TUBES

CROSS-REFERENCE TO RELATED APPLICATIONS

This application claims the benefit of Provisional Application of the same title, Ser. No. 62/113,320, filed Feb. 6, 2015.

FEDERALLY SPONSORED RESEARCH

Not Applicable

SEQUENCE LISTING OR PROGRAM

Not Applicable

FIELD OF INVENTION

The present invention relates to a laboratory tube presentation device for raising a selected row of tubes contained in a tube rack higher than the remaining rows of tubes for easy access to or tracking of individual tubes by a user.

BACKGROUND OF INVENTION

Scientific research and medical testing require the manipulation, tracking, and storing of a large number of samples; each sample contained in an individual tube. The tubes are placed in racks in an upright densely packed configuration, most commonly arranged in industry standard racks originally de-fined by the Society for Biomolecular Screening (SBS) with the outer dimensions or foot print of the rack being 127.76 mm×85.48 mm. The SBS footprint ha been widely adopted in the industry and SBS tube racks are well known in the art. The most common tube rack configuration is an orthogonal matrix of 96-wells placed in 8 rows of 12 columns. The tubes may also be arranged in a SBS staggered or diagonal matrix, now commonly referred to as the honeycomb configuration. Alterations from the preferred embodiment would be required to accommodate this configuration and are not here described. Although the SBS footprint has been widely adopted by the industry, one skilled in the art would understand that this invention would also be useful with other tube rack configurations and the SBS tube rack is used here as the preferred embodiment.

Although these tube racks provide the benefits of space saving and allow for tracking and manipulation of many samples, the densely packed tube rack configurations makes it difficult to manually remove a tube positioned in the middle of the tube rack. The inside tubes are only accessible from the top. The tubes are too densely packed to allow a user's fingers to fit between or around the individual tubes to easily pick up or remove a specific tube, particularly with smaller diameter tubes. To further complicate things, to prevent contamination, a user is often wearing nitrile or latex gloves that decrease a user's ability to feel the edges of the tubes when the tubes are placed closely together. The lower sensitivity and the fact a user's fingers cannot fit between the tubes makes it exceedingly difficult to remove or access an inside tube. Furthermore, if the tubes do not have lids, sample-to-sample contamination may occur when a user's fingers touch the tops of the surrounding tubes, or it might cause sample contamination if the tube is accidentally dropped during an unsuccessful attempt at removing a tube.

The densely packed rack configuration also makes it difficult for a user to keep track of individual tubes during experiments or other processes. The tubes are packed so densely that the tops of the tubes are all but touching one another. A user adding to or removing from individual samples may find it difficult to keep track of which tube to access. This may also cause sample-to-sample contamination or cause experimental errors due to incorrect sample preparation when a user inadvertently adds to or removes from the wrong tube.

These and other circumstances make a simple and inexpensive device to raise a single row of tubes higher than the remaining rows of tubes for easy access, a useful tool in a modern laboratory environment.

SUMMARY OF THE INVENTION

This invention relates to a laboratory tube presentation device. The preferred embodiment disclosed is a mechanical apparatus that cooperates with a standard laboratory tube rack, for example, one with 96 compartments or wells to vertically support up to 96 laboratory tubes. The tube rack is seated on the presentation apparatus, which has a hole template corresponding to the tube rack wells through which lifting pins extend to the underside of the laboratory tubes. Using a lift mechanism a row of tubes is raised by a stick shifter moved to a position alongside the row of tubes to be elevated. The mechanism does not require electrical power or electronic components and is easily and inexpensively fabricated.

BRIEF DESCRIPTION OF THE DRAWINGS

FIG. 7 is a perspective view of the lift pin assembly of FIGS. 4 and 5 removed from the displaceable selector assembly.

FIG. 8 is a perspective view of the displaceable selector assembly of FIGS. 4 and 5 with an actuator assembly removed.

DETAILED DESCRIPTION OF THE PREFERRED EMBODIMENT

Figure 1:
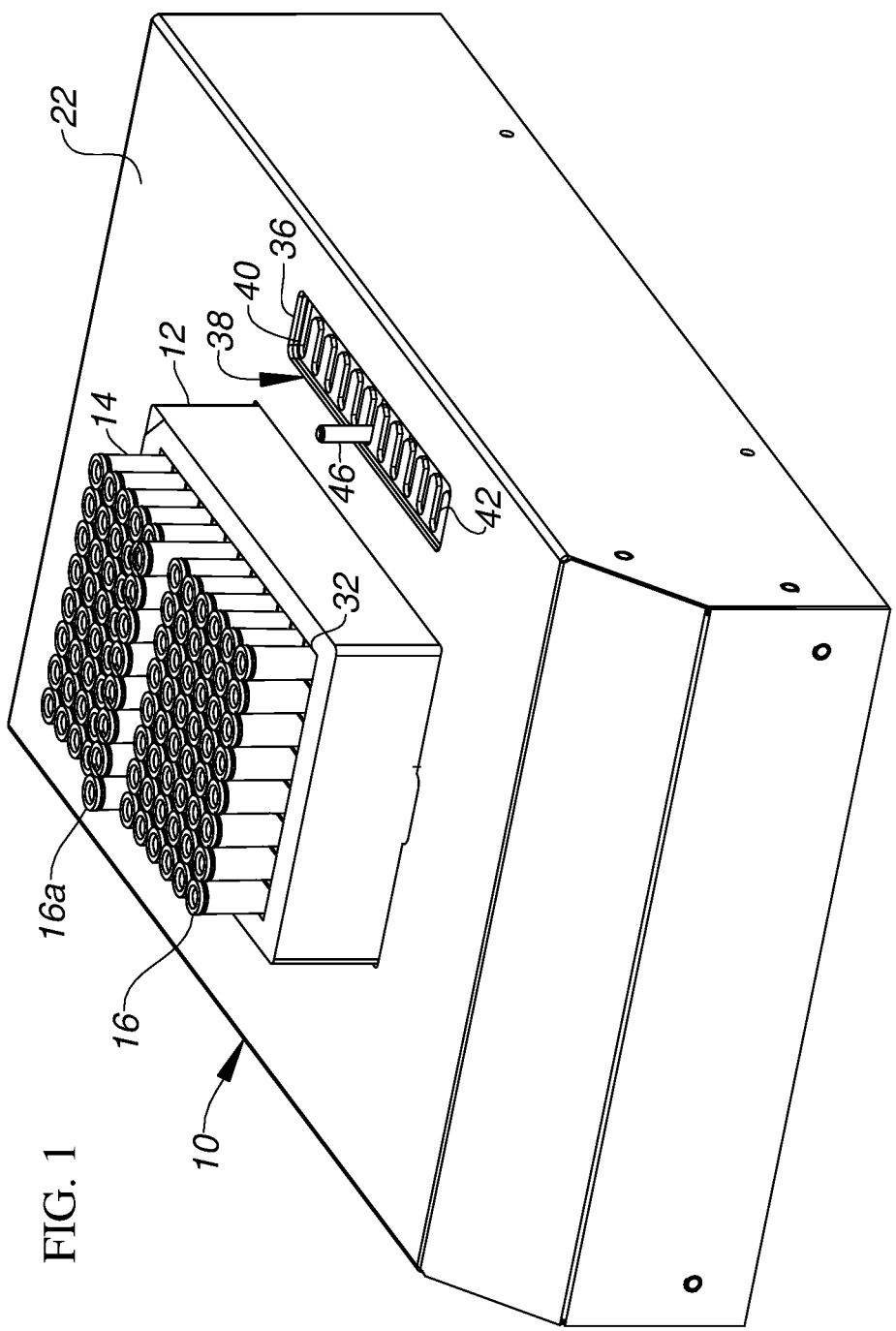
FIG. 1 is a perspective view of the laboratory tube presentation unit of this invention on which is seated a standard tube rack filled with laboratory tubes.
Figure 2:
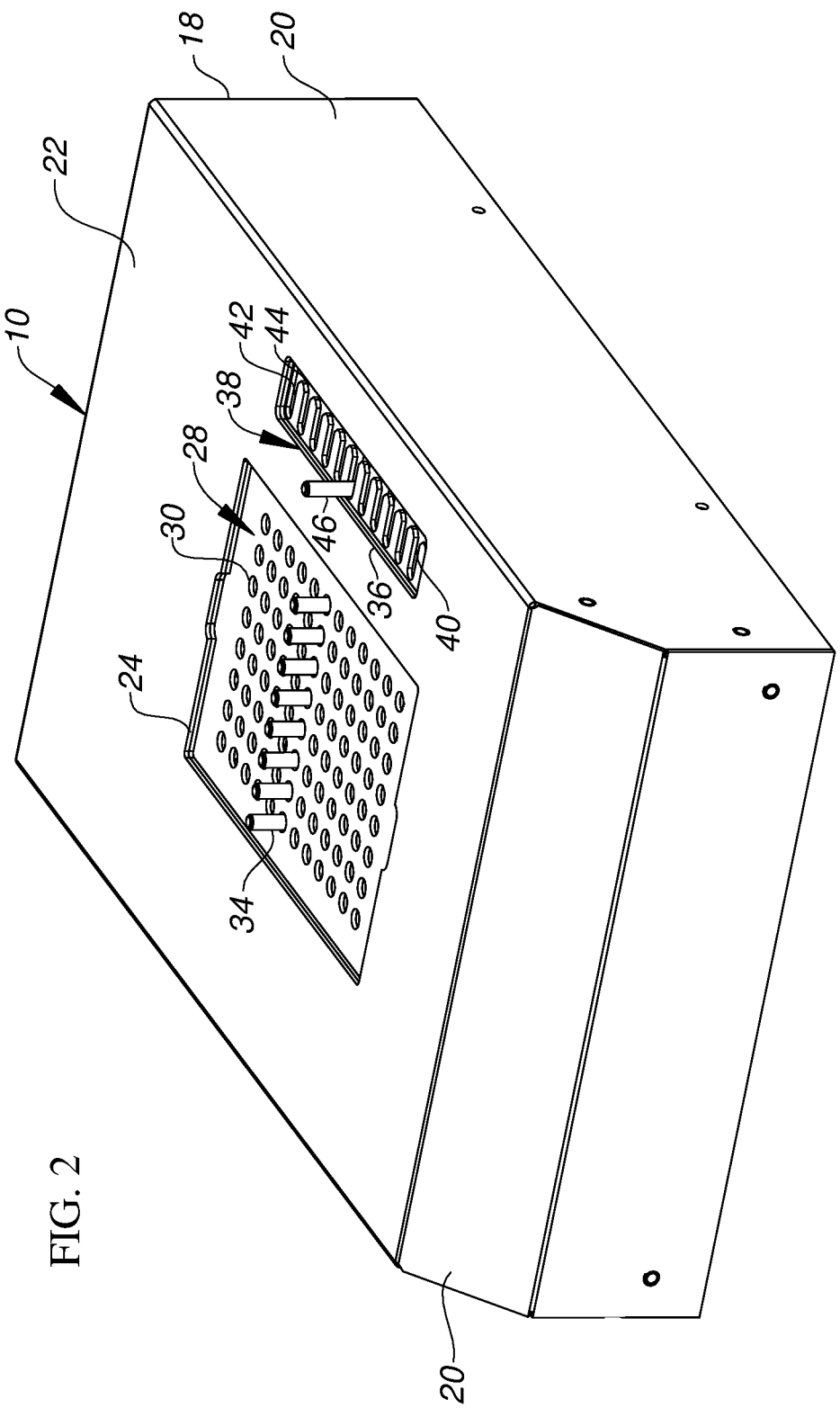
FIG. 2 is a perspective view of the laboratory tube presentation unit of FIG. 1 with the tube rack removed, showing raised lift pins that engage the bottom of a select row of laboratory tubes.
Figure 9:
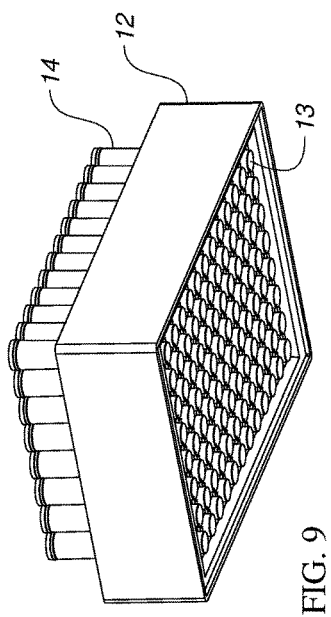
FIG. 9 is a perspective view of the underside of a tube rack of the type used in the laboratory tube presentation unit of this invention.

A preferred embodiment of the laboratory tube presentation apparatus of this invention is shown in FIGS. 1 and 2, as a laboratory tube presentation unit, designated generally by the reference numeral 10. The tube presentation unit 10 is a mechanical desktop device that is preferably designed for manual operation without electrical power or electronic components. In the perspective view of FIG. 1, the tube presentation unit 10 is shown with a conventional laboratory tube rack 12 with a plurality of laboratory tubes 14 arranged in rows 16 with one row 16a having the tubes elevated to facilitate removal, typically by the user's fingers. The conventional laboratory tube rack 12 with laboratory tubes 14 is also shown in FIG. 9.

In FIG. 2, showing the auxiliary tube rack 12 removed, the tube presentation unit 10 is constructed with a outer unit housing 18 having side enclosures 20 and a top deck 22. The top deck 22 has a central rectangular opening 24 configured to the bottom of the tube rack 12 to locate and seat the laboratory tube rack 12 on or over a tube rack support plate 26. The portion of the support plate 26 under the central opening 24 has a tube position template 28 with holes 30. The holes 30 are arranged to correspond to openings 13 in tube wells 32 of the conventional tube rack 12 of the type illustrated in FIG. 1 and FIG. 9.

Referring to FIG. 2, a series of lift pins 34 are shown raised through a row of holes 30 in the tube position template 28 of the tube rack support plate 26. The lift pins 34 engage the bottom of tubes 14 and elevate the tubes as shown in FIG. 1.

In FIGS. 1 and 2 the top deck 22 also has an elongated rectangular opening 36 along one side framing a selection guide 38 in the support plate 26. The selection guide 38 has a comb-like opening 40 with a series of selection slots 42. An elongated bus slot 44 interconnects the selection slots 42. A stick shifter 46 projects up through the opening 40 in the support plate 26 and the elongated opening 36 of the top deck 22. This interconnection of the slots 42 allows the stick shifter 46 to be moved from one slot to another by an operator. The slot location of the stick shifter 46 shown in FIGS. 1 and 2 corresponds to the row of tubes elevated in FIG. 1. It is to be understood that the stick shifter 46 can be moved to any desired slot 42 for raising the corresponding row of laboratory tubes.

Figure 3:
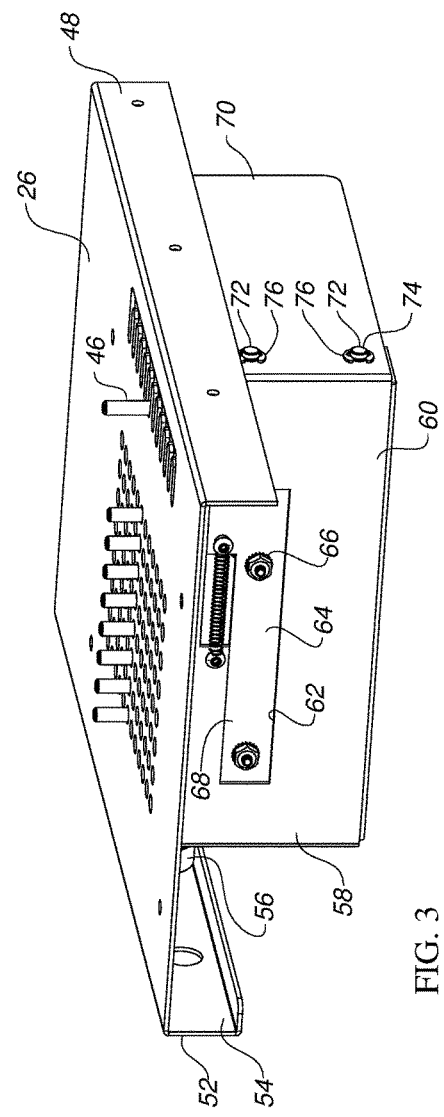
FIG. 3 is a perspective view of the laboratory tube presentation unit of FIG. 1 with an outer housing removed to show the tube rack support plate and coupled selector assembly components.
Figure 4:
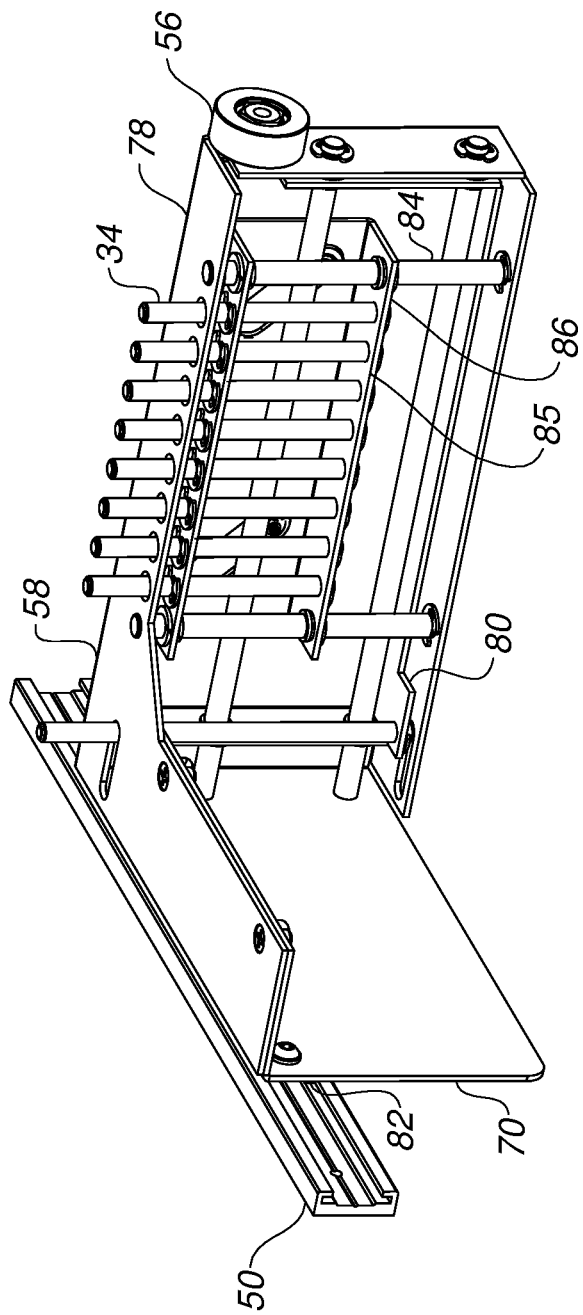
FIG. 4 is a perspective view of the displaceable selector assembly of the laboratory tube presentation unit of FIG. 1 with lift pins raised.
Figure 5:
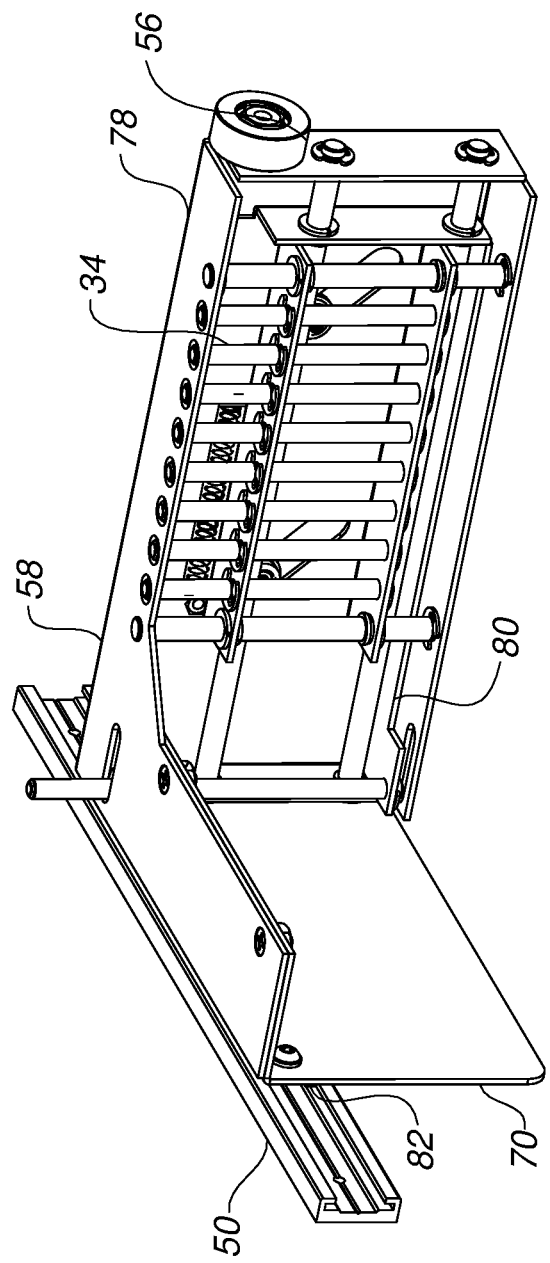
FIG. 5 is a perspective view of the displaceable selector assembly of the laboratory tube presentation unit of FIG. 1 with lift pins lowered.

As shown in FIGS. 3 to 5, the tube rack support plate 26 is fabricated of a metal sheet with one folded down side 48 that serves as a support for a horizontal bearing guide 50 and an opposite folded down side 52 that forms a guide channel 54 for an idler wheel 56. The stick shifter 46 is a component of a selector assembly 58 moveably supported between the horizontal bearing guide 50 and the guide channel 54. The tube rack support plate 26 of FIG. 3 is coupled to a displaceable selector assembly housing 60 shown with a side opening 62. The side opening 62 reveals part of an actuator assembly carriage 64. The opening is provided to accommodate a pair of projecting cam bushing mounts 66 of an actuator shuttle 68.

One side plate 70 of the selector assembly housing 58 supports parallel horizontal guide rods 72 having ends 74 with fastener clips 76. As shown in greater detail in FIGS. 4 and 5 in a flipped assembly view for clarity, the side plate 70 of the selector assembly housing 58 has an actuator support frame 78 that supports the actuator assembly 80 on slide bearings 82 that engage the horizontal bearing guide 50 attached to the folded down side 48 of the tube rack support plate 26. Together with the idler wheel 56 that tracks on the guide channel 54 of the tube rack support plate 26, the actuator assembly carriage 64 is displaceable in a linear fashion corresponding to the limitations of the elongated bus slot 44.

The actuator support frame 78 also provides a mount for vertical guide rods 84 for a pin assembly 85 with the lift pins 34 mounted in a row on a vertically displaceable shift bracket 86. The shift bracket 86 is in the form of a C-channel, as shown in FIG. 7, that is guided by the vertical guide rods 84. The shift bracket 86 has top and bottom pin holding plates 88 that mount the lift pins 34. The lift pins 34 are removable enabling only a part of a row of laboratory tubes to be elevated. A vertical back plate 90 interconnects the top and bottom pin holding plates 88.

The vertical back plate 90 has displaced inclined cam slots 92 that cooperate with a pair of displaced cam bushings 94 that are shown mounted on the back plate 96 of the actuator shuttle 68 of the actuator assembly 80 in FIG. 8.

Figure 6:
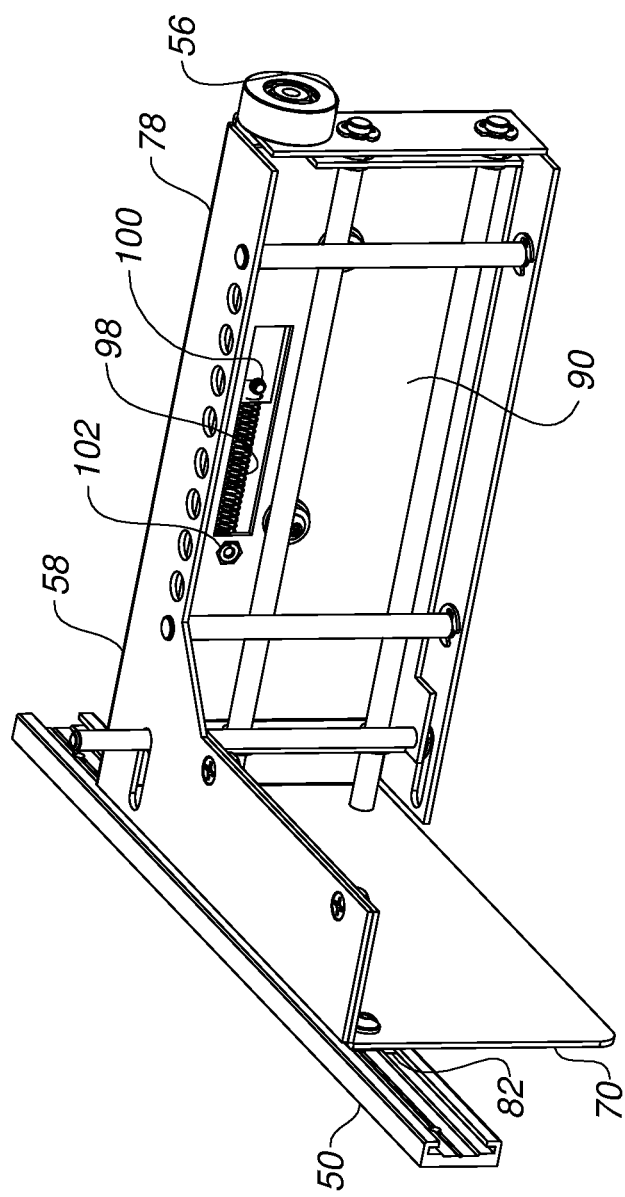
FIG. 6 is a perspective view of part of the displaceable selector assembly of FIGS. 4 and 5 with a lift pin assembly removed.

When the cam bushings 94 engage the inclined cam slots 92 and the actuator shuttle 68 is displaced on the horizontal guide rods 72 by action on the stick shifter 46, the shift bracket 86 is displaced, raising or lowering the row of lift pins 34. As shown in FIG. 6, an actuator return spring 98 connected to an anchor 100 on the selector assembly housing 58 at one end and to an anchor 102 on the vertical back plate 90 at its other end.

In this manner the actuator shuttle is biased to extending the row of lift pins 34 to maintain the elevated position of the corresponding row of laboratory tubes 14, the weight of which might otherwise cause inadvertent return of the shuttle and lowering of the tubes.

It is to be understood that modifications to the system disclosed as the preferred embodiment may be made without departing from the spirit of the invention. Modifications may also be made to accommodate racks of different size or arrangement and number of wells that accommodate different laboratory tubes.

The invention claimed is:

1. A laboratory tube presentation unit that enables removal of a selected laboratory tube in a tube rack having multiple rows of laboratory tubes by raising the row of tubes in which the tube to be selected tube is located, the rack having tube wells and a rectangular bottom with a hole in each well, the tube presentation unit comprising:
   - a housing having a top deck on which the rectangular bottom of the rack is seated, the top deck having a rectangular opening located under the rectangular bottom of a rack seated on the top deck,
   - a selector assembly having a displaceable actuator assembly with an actuator assembly carriage having a row of lift pins that are alignable under a select row of holes in the tube wells that correspond to a row of tubes having the selected tube in the tube rack when the tube rack is seated on the top deck over the rectangular opening on the top deck, the actuator assembly carriage having further an actuator with a manual transport stick shifter projecting up through the top deck that displaces the actuator assembly and a lift mechanism that raises the row of lift pins when the transport stick shifter has manually positioned the row of lift pins under the select row of holes in the tube wells having the particular tube to be removed, wherein the top deck has a series of selection slots and an interconnecting bus slot that runs along the length of the tube well holes, and wherein the transport stick shifter projects up through the top deck and is locatable in the bus slot and any one of the selection slots.

2. The laboratory tube presentation unit of claim 1 wherein the manual transport stick shifter of the actuator assembly carriage is connected to the lift mechanism and the lift mechanism includes an actuator shuttle with a lift cam that raises the actuator shuttle on displacement of the stick shifter in one of the selection slots.

3. The laboratory tube presentation unit of claim 2 wherein the lift mechanism includes a spring to bias the actuator shuttle to maintain a lift position against the weight of laboratory tubes in the row of laboratory tubes raised.

4. The laboratory tube presentation unit of claim 1 wherein the rectangular opening on the top deck has a support plate with a tube position template with holes in rows that correspond to the holes in the bottom of the tube rack when the tube rack is seated at the rectangular opening on the top deck.

5. The laboratory tube presentation unit of claim 1 wherein the housing has an internal guide track that is engaged by the actuator assembly carriage and that guides the actuator assembly carriage when displaced by the manual transport stick shifter.

6. The laboratory tube presentation unit of claim 5 wherein the top deck has a series of selection slots and an interconnecting bus slot and wherein the actuator assembly carriage is connected to the manual transport stick shifter and is displaced when the manual transport stick shifter is moved in the bus slot.

7. A laboratory tube presentation unit that enables removal of a selected laboratory tube in a tube rack having multiple rows of laboratory tubes by raising the row of tubes in which the selected tube is located, the rack having tube wells and a rectangular bottom with a hole in each well, the tube presentation unit comprising:
   an outer housing having sides and a top deck with a rectangular opening that accommodates the rectangular bottom of the rack,
   a support plate mounted under the top deck, the support plate having a tube position template with holes in rows that correspond to the holes in the bottom of the tube rack when seated in the rectangular opening on the support plate,
   a selector assembly having a displaceable actuator assembly carriage and a carriage track enabling reciprocal displacement of the actuator assembly carriage, the actuator assembly carriage having a series of lift pins that are alignable with a row of holes in the tube position plate when the displaceable actuator assembly carriage is moved to position the series of lift pins under a row of holes in the tube position plate that correspond to a row of tubes having the selected tube in the tube rack when the tube rack is mounted in the top deck opening on the support plate, the actuator assembly carriage having further an actuator mechanism with a stick shifter, wherein the top deck has a series of selection slots and an interconnecting bus slot with the stick shifter projecting up through the top deck and locatable in the bus slot and any one of the selection slots, whereupon locating the stick shifter in a selected selector slot corresponding to a tube row, the actuator mechanism raises the tube row and facilitates access to the selected tube.

8. The laboratory tube presentation unit of claim 7 including a cam lift, wherein upon moving the displaceable actuator assembly to position the series of lift pins under a row of holes in the position template, the actuator mechanism connected to the stick shifter engages the cam lift and raises the lift pins on moving the stick shifter into a selected selection slot.

9. The laboratory tube presentation unit of claim 8 wherein the actuator mechanism cooperates with a spring to retain the raised lift pins until the stick shifter is retracted from the selected selection slot.

* * * * *